United States Patent [19]
Denzel et al.

[11] 3,987,051
[45] Oct. 19, 1976

[54] METHOD FOR PRODUCING 1-UNSUBSTITUTED PYRAZOLO[3,4-b]PYRIDINE KETONES

[75] Inventors: Theodor Denzel; Hans Joachim Schneider, both of Regensburg; Hans Hoehn, Tegernheim, all of Germany

[73] Assignee: E. R. Squibb & Sons, Inc., Princeton, N.J.

[22] Filed: Apr. 16, 1975

[21] Appl. No.: 568,755

[52] U.S. Cl. .................. 260/296 H; 260/250 AH; 260/256.4 R; 260/268 BC; 260/293.6; 260/295.5 B
[51] Int. Cl.² ....................................... C07D 471/04
[58] Field of Search .............. 260/296 H, 295.5 B, 260/250 AH, 256.4 R, 268 BC, 293.6

[56] References Cited
OTHER PUBLICATIONS

Wiley, "Pyrazoles, Pyrazolines etc.," (1967), pp. 73 & 74.

*Primary Examiner*—Henry R. Jiles
*Assistant Examiner*—R. W. Ramsuer
*Attorney, Agent, or Firm*—Lawrence S. Levinson; Merle J. Smith

[57] ABSTRACT

A new process for the production of pyrazolo-[3,4-b]pyridine ketones which are unsubstituted in the 1-position comprises reacting a 1-furanylmethyl-pyrazolo[3,4-b]pyridine ketone with an inorganic strong mineral acid like sulfuric acid, phosphoric acid or polyphosphoric acid.

11 Claims, No Drawings

METHOD FOR PRODUCING 1-UNSUBSTITUTED PYRAZOLO[3,4-B]PYRIDINE KETONES

SUMMARY OF THE INVENTION

This invention relates to an improved process for the production of pyrazolo[3,4-b]pyridine-5-ketones, unsubstituted in the 1-position, which comprises reacting a 1-furanylmethylpyrazolo[3,4-b]pyridine-5-ketone with a strong inorganic mineral acid such as sulfuric acid, phosphoric acid or polyphosphoric acid to remove the furanylmethyl group and provide a product unsubstituted in the 1-position.

DETAILED DESCRIPTION OF THE INVENTION

U.S. Pat. No. 3,828,057, Aug. 9, 1974, describes a group of pyrazolo[3,4-b]pyridine-5-ketones which are useful as central nervous system depressants and antiinflammatory agents. These compounds have the formula

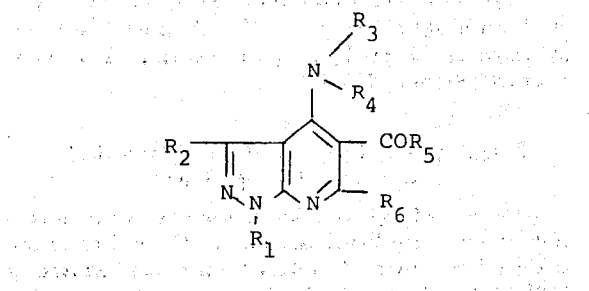

wherein the symbols are defined as $R_1$ is hydrogen, lower alkyl, phenyl or phenyl-lower alkylene, benzoyl or substituted benzoyl. $R_2$ is hydrogen or lower alkyl. The basic nitrogen group

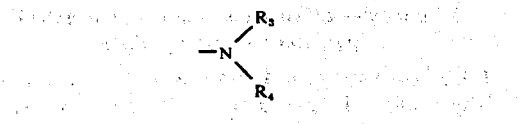

is an acyclic amino moiety wherein $R_3$ and $R_4$ each is hydrogen, lower alkyl, lower alkanoyl, cyclo-lower alkyl, halo-lower alkanoyl, phenyl, substituted phenyl, phenyl-lower alkylene, amino-lower alkylene or di-lower alkyl-amino-lower alkylene or $R_3$ and $R_4$ complete a heterocycle of 3,5- or 6-members in which an additional nitrogen is present, i.e., the aziridinyl, pyrrolidino, piperidino, pyrazolyl, pyrimidinyl, pyridazinyl or piperazinyl radicals each of which may also bear as a substituent a hydroxy-lower alkyl group or one or two lower alkyl groups.

$R_5$ is alkyl of up to 10 carbon atoms, lower alkyl, cycloalkyl, phenyl or substituted phenyl.

$R_6$ is hydrogen or lower alkyl.

According to said patent, the pyrazolo[3,4-b]pyridine-5-ketones involved are produced from 5-aminopyrazoles having the $R_1$ and $R_2$ substituents desired in the final product. This starting material is made to react with an alkoxymethylene aroyl acetic acid ester or alkanoyl acetic acid ester and the product of this reaction is then cyclized to obtain the pyrazolo[3,4-b]pyridine structure. Certain other reactions are then carried out involving the 4- and/or 5- positions to obtain the product with the desired substituents in those positions.

In the case of compounds which have the above formula wherein $R_1$ is hydrogen, however, the general process is modified. According to the modification, the starting material is a 5-aminopyrazole having in the 1-position an arylmethyl or heteromethyl group like furanylmethyl, pyridylmethyl, etc. This starting material is processed in the same manner as other starting material. At one of the late stages of the synthesis, the arylmethyl or heteromethyl group in the 1-position is removed with an oxidizing agent like selenium dioxide in a high boiling solvent. The product, unsubstituted in the 1-position, is thus obtained.

Selenium dioxide is an expensive reagent and is difficult to separate at the completion of the reaction. Moreover, when $R_5$ in the above formula is an alkyl group, the yields are low. All of these factors adversely affect the economics of the process.

It has now been found that the process for making 1-unsubstituted pyrazolo[3,4-b]pyridine-5-ketones can be markedly improved by utilizing a pyrazolo[3,4-b]pyridine-5-ketone with a furanylmethyl group in the 1-position and removing the furanylmethyl group with a strong inorganic acid like phosphoric acid, polyphosphoric acid or sulfuric acid.

This invention therefore comprises an improved process for producing certain of the pyrazolo[3,4-b]pyridine-5-ketones found in the patent cited above. The compounds resulting from the process of this invention have the formula (I)

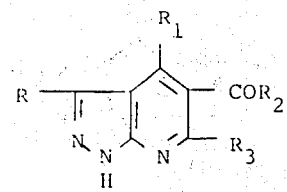

wherein R is hydrogen or lower alkyl; $R_1$ is lower alkoxy or the group

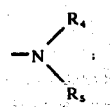

$R_2$ is lower alkyl, cyclo-lower alkyl, phenyl or substituted phenyl wherein the phenyl substituent is halo, lower alkyl or lower alkoxy; $R_3$ is hydrogen, lower alkyl or phenyl; and $R_4$ and $R_5$ each is hydrogen, lower alkyl, cyclo-lower alkyl, phenyl or phenyl-lower alkyl or together $R_4$ and $R_5$ join to complete a 5- or 6-membered heterocyclic of the group pyrrolidine, piperidine, pyrimidine, pyridazine or piperazine.

The lower alkyl and lower alkoxy groups in any of the foregoing radicals include straight or branched chain hydrocarbon groups of one to seven carbon atoms like methyl, ethyl, propyl, isopropyl, butyl, t-butyl and the like. The $C_1$-$C_4$ members are preferred. Benzyl and phenethyl are the preferred phenyl-lower alkylene groups. All four halogens are included, but chlorine is preferred.

The cycloalkyl groups are the three to seven carbon alicyclics cyclopropyl, cyclobutyl, cyclopentyl, cyclohexyl and cycloheptyl of which the $C_5$- and $C_6$-membered rings are preferred.

The basic nitrogen group

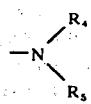

is an acyclic amino group wherein $R_4$ and $R_x$ each is hydrogen, lower alkyl, phenyl or phenyl-lower alkyl (preferably there is only one of these substituents other than lower alkyl). This basic group may also form a heterocycle of 5- or 6-members in which an additional nitrogen is present, in particular, pyrrolidino, piperidino, pyrimidinyl, pyridazinyl or piperazinyl radicals.

The products shown in the examples are representative of the compounds with which this invention is concerned and constitute preferred embodiments. Especially preferred products produced by the method of this invention are those compounds of formula I wherein R and $R_3$ each is hydrogen; $R_1$ is lower alkoxy, especially ethoxy, or lower alkylamino, especially butylamino; and $R_2$ is lower alkyl, especially methyl or ethyl, or phenyl.

According to the process of this invention a compound of the formula (II)

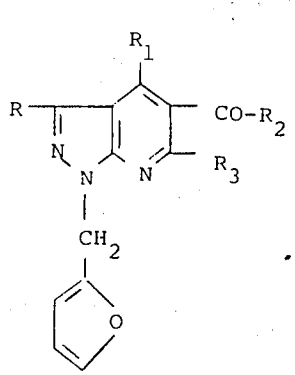

wherein the symbols have the same meaning as above, is treated with a strong inorganic acid like phosphoric, polyphosphoric or sulfuric acid, preferably at an elevated temperature, e.g., 30° to 90° C. Highly concentrated acid in excess of 90% concentration is used. The acid can also serve as the reaction medium. An excess of the acid is used, e.g., a proportion of about 3 to 20 parts of acid per part of compound to be treated, but preferably the amount of acid used is at the low end of the range in order to minimize the amount to be neutralized later.

The reaction is normally complete within a period of about 1 to 12 hours. Upon completion of the reaction, the mixture is diluted with water to hydrolyze the salt and liberate the free base and this is filtered to remove insoluble by-products. Addition of a base which forms a highly soluble salt with the anion of the mineral acid used, e.g., ammonia (which is preferred), sodium hydroxide, potassium hydroxide or the like whose sulfates, phosphates, etc. are very water soluble, neutralizes any remaining acid and usually results in the precipitation of the product which can then be isolated.

The starting materials for the present process are produced as described in U.S. Pat. No. 3,828,057, Aug. 6, 1974, and U.S. Pat. No. 3,855,675, Dec. 24, 1974, and the products obtained are useful as central nervous system depressants and anti-inflammatory agents as described in the first of these.

The following examples are illustrative of the invention and serve as models for the production of other products within the scope of this invention. All temperatures are in degrees celsius.

EXAMPLE 1 a.

[[[1-(2-furanyl)methylpyrazolyl]amino]methylene]-benzoyl acetic acid, ethyl ester 163 g. of 1-(2-furanyl)methyl-5-aminopyrazole (1 mol.) and 248 g. of ethoxymethylene benzoyl acetic acid, ethyl ester (1 mol.) are heated at 130° until no more alcohol distils off (approx. 1 hour). The oily residue crystallizes and yields, on cooling and recrystallizing from hexane, 310 g. of [[[1-(2-furanyl)methyl-5-pyrazolyl]amino]methylene]benzoyl acetic acid, ethyl ester (85%), m.p. 75°–77°.

b.

5-benzoyl-4-hydroxy-1-(2-furanyl)methyl-1H-pyrazolo-[3,4-b]pyridine 36.5 g. of [[[1-(2-furanyl)methyl-5-pyrazolyl]-amino]methylene]benzoylacetic acid, ethyl ester are dissolved in 50 ml. of diphenyl ether and refluxed at 260° for 30 minutes. Distillation of the solvent yields a dark oil which crystallizes on addition of methanol. Recrystallization yields 20 g. of 5-benzoyl-4-hydroxy-1-(2-furanyl)methyl-1H-pyrazolo[3,4-b]pyridine (61%), m.p. 102°.

c.

5-benzoyl-4-ethoxy-1-(2-furanyl)methyl-1H-pyrazolo[3,4-b]-pyridine 3.3 g. of 5-benzoyl-4-hydroxy-1-(2-furanyl)methyl-1H-pyrazolo[3,4-b]pyridine (0.01 mol.) are dissolved in 20 ml. of dimethylformamide. 2.8 g. of potassium carbonate and 3.1 g. of ethyl iodide are added and the mixture is warmed for 12 hours at 60°. Excess potassium carbonate is filtered off and water is added. 5-Benzoyl-4-ethoxy-1-(2-furanyl)-methyl-1H-pyrazolo[3,4-b]pyridine precipitates and is recrystallized from ethyl acetate, yield 3 g. (86%), m.p. 70°.

d. 5-benzoyl-4-ethoxy-1H-pyrazolo[3,4-b]pyridine 34.7 g. of 5-benzoyl-4-ethoxy-1-(2-furanyl)methyl-1H-pyrazolo[3,4-b]pyridine (0.1 mol.) are dissolved in 200 ml. of polyphosphoric acid at 60° with continuous stirring. Heating and stirring is maintained for 12 hours. The dark mixture is then poured into 500 ml. of ice water and filtered. The filtrate is made alkaline by adding 30% aqueous ammonia. 5-Benzoyl-4-ethoxy-1H-pyrazolo[3,4-b]pyridine precipitates and is filtered off, yield 13.9 g. (52%), m.p. 202°–203° (butanol).

EXAMPLE 2

5-Benzoyl-4-ethoxy-1H-pyrazolo[3,4-b]pyridine 87 g. of 5-benzoyl-4-ethoxy-1-(2-furanyl)methyl-1H-pyrazolo[3,4-b]pyridine (0.25 mol.) are dissolved in 300 ml. of conc. sulfuric acid within 15 to 20 minutes with vigorous stirring. The temperature rises to 40°–45°. Stirring is continued for 1 hour. The dark colored mixture is then added to 3700 ml. of cold water. Stirring is continued for 2 hours and the dark by-products are filtered off. The filtrate is made alkaline with 25% aqueous ammonia. The white precipitate of 5-benzoyl-4-ethoxy-1H-pyrazolo[3,4-b]pyridine is filtered off, yield 44.8 g. (66%), m.p. 202°–203° (butanol).

EXAMPLE 3 a.

[[[1-(2-furanyl)methylpyrazolyl]amino]methylene]acetoacetic acid ethyl ester 163 g. of 1-(2-furanyl)methyl-5-aminopyrazole (1 mol.) is treated with 186 g. of ethoxymethylene acetoacetic acid, ethyl ester (1 mol.) at 120° with continuous stirring for 45 minutes. The alcohol formed is distilled off in vacuo and the oily residue is crystallized with 500 ml. of diethyl ether to obtain [[[1-(2-furanyl)methylpyrazolyl]amino]methylene]-acetoacetic acid ethyl ester, yield 260 g. (86%), m.p. 93°–94° (methanol).

b.

5-acetyl-1-(2-furanyl)methyl-4-hydroxy-1H-pyrazolo[3,4-b]pyridine 30.3 g. of [[[1-(2-furanyl)methylpyrazolyl]amino]-methylene-]acetoacetic acid, ethyl ester (0.1 mol.) is heated at 250° for 8 minutes. The dark oil is cooled and dissolved in 50 ml. of methanol. 5-Acetyl-1-(2-furanyl)methyl-4-hydroxy-1H-pyrazolo[3,4-b]pyridine crystallizes and is filtered off, yield 17 g. (64%), m.p. 108°–110° (methanol).

c.

5-acetyl-4-ethoxy-1-(2-furanyl)methyl-1H-pyrazolo[3,4-b]pyridine 2.8 g. of 5-acetyl-4-ethoxy-1-(2-furanyl)methyl-1H-pyrazolo[3,4-b]pyridine (0.05 mol.) are treated with 8 g. of ethyl iodide and 14 g. of potassium carbonate in 50 ml. of dimethylformamide at 60° for 12 hours. The mixture is cooled, the inorganic precipitate is filtered off and the filtrate evaporated to dryness. The oily residue is crystallized with methanol to obtain 5-acetyl-4-ethoxy-1-(2-furanyl)methyl-1H-pyrazolo[3,4-b]pyridine, yield 10.8 g. (75%), m.p. 139°–141° (methanol).

d. 5-acetyl-4-ethoxy-1H-pyrazolo[3,4-b]pyridine 2.8 g. of 5-acetyl-4-ethoxy-1-(2-furanyl)methyl-1H-pyrazolo[3,4-b]pyridine (0.01 mol.) are treated with 10 ml. of polyphosphoric acid with stirring at 60° for 12 hours. After this time, the mixture is decomposed with 30 ml. of water and filtered. The filtrate is made alkaline with 30% aqueous ammonia. 5-Acetyl-4-ethoxy-1H-pyrazolo[3,4-b]-pyridine precipitates, yield 1.2 g. (58%), m.p. 245°–248° (butanol).

EXAMPLE 4 a.

5-benzoyl-4-sec.butylamino-1-(2-furanyl)methyl-1H-pyrazolo-[3,4-b]pyridine 34.7 g. of 5-benzoyl-4-ethoxy-1-(2-furanyl)methyl-1H-pyrazolo[3,4-b]pyridine (0.1 mol.) is refluxed for 10 hours with 50 ml. of sec. butylamine. The excess amine is removed in vacuo and the residue recrystallized from methanol to obtain 5-benzoyl-4-sec.-butylamino-1-(2-furanyl)methyl-1H-pyrazolo[3,4-b]pyridine, yield 31 g. (83%), m.p. 112°–114° (methanol).

b.

5-benzoyl-4-sec.butylamino-1H-pyrazolo[3,4-b]pyridine 3.7 g. of 5-benzoyl-4-sec.butylamino-1-(2-furanyl)-methyl-1H-pyrazolo[3,4-b]pyridine are stirred in 20 ml. of conc. sulfuric acid for 3 hours at 50°. The mixture is decomposed with 30 ml. of water and filtered. The filtrate is made alkaline with 30% aqueous ammonia and the white precipitate of 5-benzoyl-4-sec.-butylamino-1H-pyrazolo[3,4-b]-pyridine is filtered off, yield 1.7 g. (58%), m.p. 186°–187°.

EXAMPLE 5

4-Amino-5-benzoyl-3-methyl-1H-pyrazolo[3,4-b]pyridine 4-amino-5-benzoyl-3-methyl-1-(2-furanylmethyl)-1H-pyrazolo[3,4-b]pyridine is treated with concentrated sulfuric acid according to the procedure of Example 4 b to obtain 4-amino-5-benzoyl-3-methyl-1H-pyrazolo[3,4-b]pyridine.

EXAMPLE 6

5-(3-Chlorobenzoyl)-4-methoxy-6-methyl-1H-pyrazolo[3,4-b]pyridine 5-(3-Chlorobenzoyl)-1-(2-furanylmethyl)-4-methoxy-6-methyl-1H-pyrazolo[3,4-b]pyridine is treated with concentrated phosphoric acid according to the procedure of Example 1d to obtain 5-(3-chlorobenzoyl)-4-methoxy-6-methyl-1H-pyrazolo-[3,4-b]pyridine.

EXAMPLE 7

5-(p-Methylbenzoyl)-4-dimethylamino-3-ethyl-1H-pyrazolo-[3,4-b]pyridine

4-Dimethylamino-3-ethyl-1-(2-furanyl)methyl-5-(p-methylbenzoyl)-1H-pyrazolo[3,4-b]pyridine is treated with polyphosphoric acid according to the procedure of Example 2 to obtain 5-(p-methylbenzoyl)-4-dimethylamino-3-ethyl-1H-pyrazolo[3,4-b]pyridine.

EXAMPLE 8

5-Cyclohexanecarbonyl-4-ethoxy-1H-pyrazolo[3,4-b]pyridine

5-Cyclohexanecarbonyl-4-ethoxy-1-(2-furanyl)-methyl-1H-pyrazolo[3,4-b]pyridine is treated with polyphosphoric acid according to the procedure of Example 1 d to obtain 5-cyclohexanecarbonyl-4-ethoxy-1H-pyrazolo[3,4-b]pyridine.

EXAMPLE 9

5-Acetyl-4-piperidino-1H-pyrazolo[3,4-b]pyridine

5-Acetyl-1-(2-furanyl)methyl-4-piperidino-1H-pyrazolo[3,4-b]pyridine is treated with concentrated sulfuric acid according to the procedure in Example 4 to obtain 5-acetyl-4-piperidino-1H-pyrazolo[3,4-b]pyridine.

EXAMPLE 10

5-Propionyl-4-pyrrolidino-1H-pyrazolo[3,4-b]pyridine 1-(2-Furanyl)methyl-5-propionyl-4-pyrrolidino-1H-pyrazolo[3,4-b]pyridine is treated with polyphosphoric acid according to the procedure of Example 3 d to obtain 5-propionyl-4-pyrrolidino-1H-pyrazolo[3,4-b]pyridine.

EXAMPLE 11

5-Benzoyl-3-methyl-4-(1-piperazinyl)-1H-pyrazolo[3,4-b]pyridine

5-Benzoyl-1-(2-furanyl)methyl-3-methyl-4-piperazinyl-1H-pyrazolo[3,4-b]pyridine is treated with concentrated sulfuric acid according to the procedure of Example 4 to obtain 5-benzyl-3-methyl-4-(1-piperazinyl)-1H-pyrazolo[3,4-b]-pyridine.

5-Benzoyl-4-(1-pyrimidinyl)-1H-pyrazolo[3,4-b]pyridine and 5-benzoyl-4-(1-pyrimidazinyl)-1H-pyrazolo[3,4-b]pyridine, respectively, are similarly obtained from their 1-(2-furanyl)-methyl analogs.

EXAMPLE 12

4-Ethylamino-5-(p-methoxybenzoyl)-6-phenyl-1H-pyrazolo[3,4-b]pyridine

4-Ethylamino-1-(2-furanyl)methyl-5-(p-methoxybenzoyl)-6-phenyl-1H-pyrazolo[3,4-b]pyridine is treated with polyphosphoric acid according to the procedure of Example 1 d to obtain 4-ethylamino-5-(p-methoxybenzoyl)-6-phenyl-1H-pyrazolo[3,4-b]pyridine.

EXAMPLE 13

5-Acetyl-4-cyclopentylamino-3-methyl-1H-pyrazolo[3,4-b]pyridine

5-Acetyl-4-cyclopentylamino-1-(2-furanyl)methyl-3-methyl-1H-pyrazolo[3,4-b]pyridine is treated with concentrated phosphoric acid according to the procedure of Example 2 to obtain 5-acetyl-4-cyclopentylamino-3-methyl-1H-pyrazolo[3,4-b]-pyridine.

EXAMPLE 14

5-Benzoyl-4-n-butylamino-6-phenyl-1H-pyrazolo[3,4-b]pyridine

5-Benzoyl-1-(2-furanyl)methyl-4-n-butylamino-6-phenyl-1H-pyrazolo[3,4-b]pyridine is treated with concentrated sulfuric acid according to the procedure of Example 4 to obtain 5-benzoyl-4-n-butylamino-6-phenyl-1H-pyrazolo[3,4-b]pyridine.

EXAMPLE 15

4-Anilino-5-benzoyl-6-methyl-1H-pyrazolo[3,4-b]pyridine

4-Anilino-5-benzoyl-1-(2-furanyl)methyl-6-methyl-1H-pyrazolo[3,4-b]pyridine is treated with polyphosphoric acid according to the procedure of Example 1 d to obtain 4-anilino-5-benzoyl-6-methyl-1H-pyrazolo[3,4-b]pyridine.

EXAMPLE 16

5-Acetyl-4-phenethylamino-1H-pyrazolo[3,4-b]pyridine

5-Acetyl-1-(2-furanyl)methyl-4-phenethylamino-1H-pyrazolo[3,4-b]pyridine is treated with polyphosphoric acid according to the procedure of Example 3 d to obtain 5-acetyl-4-phenethylamino-1H-pyrazolo[3,4-b]pyridine.

EXAMPLE 17

5-Butyryl-4-ethoxy-1H-pyrazolo[3,4-b]pyridine

5-Butyryl-4-ethoxy-1-(2-furanyl)methyl-1H-pyrazolo-[3,4-b]pyridine is treated with polyphosphoric acid according to the procedure of Example 3 d to obtain 5-butyryl-4-ethoxy-1H-pyrazolo[3,4-b]pyridine.

EXAMPLE 18

5-Benzoyl-4-butyloxy-1H-pyrazolo[3,4-b]pyridine

5-Benzoyl-4-butyloxy-1-(2-furanyl)methyl-1H-pyrazolo[3,4-b]pyridine is treated with concentrated sulfuric acid according to the procedure of Example 4 b to obtain 5-benzoyl-4-butyloxy-1H-pyrazolo[3,4-b]pyridine.

What is claimed is:

1. A process for the production of a compound of the formula

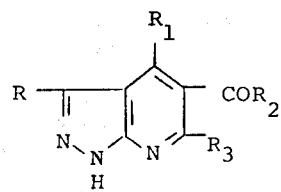

wherein R is hydrogen or lower alkyl; $R_1$ is lower alkoxy or

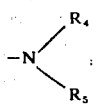

$R_2$ is lower alkyl, cyclo-lower alkyl, phenyl or substituted phenyl wherein the phenyl substituent is halo, lower alkyl or lower alkoxy;

$R_3$ is hydrogen, lower alkyl or phenyl; and $R_4$ and $R_5$ each is hydrogen, lower alkyl, cyclo-lower alkyl, phenyl or phenyl-lower alkyl or together $R_4$ and $R_5$ join to form piperidine, pyrimidine, pyrazine or piperazine, which comprises reacting a compound of the formula

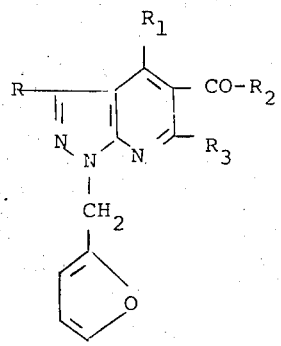

with about 3 to 20 parts of a strong inorganic acid at a temperature of about 30° to 90° C., neutralizing the reaction product with base and isolating the product from the reaction mixture.

2. A process as in claim 1 wherein the acid is sulfuric acid, phosphoric acid or polyphosphoric acid.

3. A process as in claim 1 wherein the acid is sulfuric acid.

4. A process as in claim 1 wherein the acid is polyphosphoric acid.

5. A process as in claim 1 wherein in the starting material and the product R and $R_3$ each is hydrogen and $R_1$ is lower alkoxy.

6. A process as in claim 1 wherein in the starting material and the product R and $R_3$ each is hydrogen and $R_1$ is lower alkylamino.

7. A process as in claim 1 wherein in the starting material and the product $R_2$ is lower alkyl.

8. A process as in claim 1 wherein in the starting material and final product $R_2$ is phenyl.

9. A process for the production of 5-benzoyl-4-ethoxy-1H-pyrazolo[3,4-b]pyridine which comprizes reacting 5-benzoyl-4-ethoxy-1-(2-furanyl)methyl-1H-pyrazolo[3,4-b]pyridine with about 3 to 20 parts of polyphosphoric acid or sulfuric acid at a temperature of about 30° to 90° C., neutralizing the reaction product with base and isolating the product.

10. A process for the production of 5-acetyl-4-ethoxy-1H-pyrazolo[3,4-b]pyridine which comprises reacting 5-acetyl-4-ethoxy-1-(2-furanyl)methyl-1H-pyrazolo[3,4-b]pyridine with about 3 to 20 parts of polyphosphoric acid at a temperature of about 30° to 90° C., neutralizing the reaction product with base and isolating the product.

11. A process for the production of 5-benzoyl-4-sec. butylamino-1H-pyrazolo[3,4-b]pyridine which comprises reacting 5-benzoyl-4-sec. butylamino-1-(2-furanyl)methyl-1H-pyrazolo[3,4-b]pyridine with about 3 to 20 parts of sulfuric acid, neutralizing the reaction product with base and isolating the product.

* * * * *